(12) United States Patent
Handfield, Jr. et al.

(10) Patent No.: US 7,285,686 B2
(45) Date of Patent: Oct. 23, 2007

(54) PROCESS FOR THE PREPARATION OF 1,3-SUBSTITUTED INDENES

(75) Inventors: Robert Eugene Handfield, Jr., East Lyme, CT (US); Timothy J. N. Watson, Waterford, CT (US); Phillip James Johnson, North Stonington, CT (US); Peter Robert Rose, Ledyard, CT (US)

(73) Assignee: Pfizer Inc, New York, NY (US)

( * ) Notice: Subject to any disclaimer, the term of this patent is extended or adjusted under 35 U.S.C. 154(b) by 6 days.

(21) Appl. No.: 10/714,735

(22) Filed: Nov. 17, 2003

(65) Prior Publication Data

US 2005/0004379 A1    Jan. 6, 2005

Related U.S. Application Data

(60) Provisional application No. 60/429,029, filed on Nov. 25, 2002.

(51) Int. Cl.
*C07C 43/30* (2006.01)

(52) U.S. Cl. ........................................ 568/592; 568/591

(58) Field of Classification Search ................ 549/451, 549/453, 454, 455, 545; 558/303, 311; 568/591, 568/592

See application file for complete search history.

(56) References Cited

U.S. PATENT DOCUMENTS

| 6,410,550 | B1 | 6/2002 | Coe et al. ................ 514/289 |
| 6,605,610 | B1 | 8/2003 | Coe et al. ................ 514/250 |
| 6,897,310 | B2 | 5/2005 | Coe et al. ................ 544/343 |
| 6,951,938 | B2 | 10/2005 | Coe et al. ................ 544/343 |
| 7,091,372 | B2 | 8/2006 | Singer et al. ............ 560/18 |
| 7,186,870 | B2 | 3/2007 | Singer et al. ............ 585/27 |
| 2003/0060624 | A1* | 3/2003 | Singer ..................... 544/59 |

FOREIGN PATENT DOCUMENTS

| WO | 2004046077 | 6/2004 |
| WO | 2004063164 | 7/2004 |

* cited by examiner

*Primary Examiner*—Taylor Victor Oh
(74) *Attorney, Agent, or Firm*—Steve T. Zelson; A. David Joran

(57) ABSTRACT

An improved process for the preparation of 1,3 substituted indenes which are useful intermediates in the synthesis of aryl fused azapolycyclic compounds as agents for the treatment of neurological and psychological disorders.

9 Claims, No Drawings

PROCESS FOR THE PREPARATION OF 1,3-SUBSTITUTED INDENES

BACKGROUND OF THE INVENTION

The present invention relates to an improved process for the preparation of 1,3-substituted indenes of the formula I

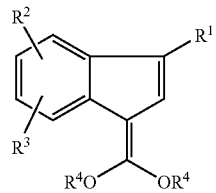

wherein $R^1$, $R^2$, $R^3$ and $R^4$ are as defined below.

Compounds of formula I are useful intermediates in the preparation of certain aryl fused azapolycyclic compounds which exhibit activity as agents for the treatment of neurological and psychological disorders.

U.S. patent application Ser. No. 09/514002 filed Feb. 25, 2000 discloses the preparation of 3-aminomethyl-indan-1-carboxylic acid methyl ester and the use of that compound as an intermediate in the synthesis of certain aryl fused azapolycyclic compounds.

U.S. patent application Ser. No. 10/124,135 filed April 04, 2002 discloses the preparation of aryl-fused azapolycyclic compounds from intermediates having the formula I.

The synthesis, composition, and methods of use of certain aryl fused azapolycyclic compounds which exhibit activity as agents for the treatment of neurological and psychological disorders is disclosed in U.S. Pat. No. 6,410,550 B1. The foregoing patent applications and patent are incorporated by reference herein in their entirety.

SUMMARY OF THE INVENTION

The present invention provides an improved process for preparing a compound of the formula I

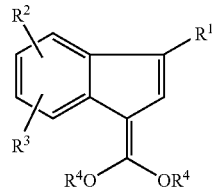

by conducting a solvent-free reaction between a compound of the formula II

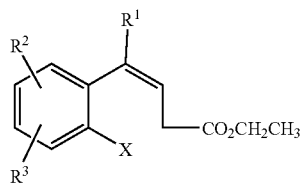

and an alcohol in the presence of sulfuric acid. The alcohol is a monohydric alcohol of the formula $R^4OH$ or a dihydric alcohol selected from the group consisting of ethylene glycol, 1,3 propylene glycol, and 1,2propylene glycol.

In a preferred embodiment, the alcohol is a dihydric alcohol. Preferably the dihydric alcohol is ethylene glycol.

As used herein, the term, solvent-free, refers to the complete absence of an inert organic solvent.

Compounds having the formula II are prepared by reacting a compound of formula III

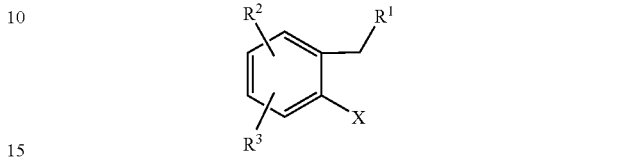

with ethyl 3-ethoxyacrylate in an inert water miscible organic solvent. The reaction is catalyzed by a mixture of palladium II acetate, tricyclohexylphosphine, and a base. Upon completion of the reaction, the inert water miscible organic solvent is completely removed. In a preferred embodiment the solvent is removed by distillation.

With reference to compounds of the formulas I, II, and III above, $R^1$ is an electron withdrawing group selected from the group consisting of cyano, alkoxy carbonyl, alkylcarbonyl, arylcarbonyl, aryl, trifluoromethyl, and sulfonyl. $R^2$ and $R^3$ are selected independently from hydrogen, $C_1$ to $C_5$ alkyl, $C_1$ to $C_5$ alkoxy, trifluoromethyl, halogen, sulfonyl, alkyl, alkylamino, amide, ester, aryl-alkyl, hetero-alkyl and aryl-alkoxy. Also, $R^2$ and $R^3$ together with the carbon atoms to which they are attached can form a monocyclic or bicyclic ring. $R^4$ is $C_1$ to $C_6$ alkyl or two $R^4$ groups together form a $C_2$ to $C_3$ alkylene bridge.

In the preparation of compounds having the formula II, the preferred catalyst is comprised of a mixture of palladium II acetate and tricyclohexylphosphine. Suitable bases are alkoxides of Group I metals. Preferably the base is sodium t-butoxide. Suitable inert water miscible organic solvents are tetrahydrofuran, 2-methyltetrahydrofuran, and 1,2-dimethoxyethane.

Preferably the solvent is tetrahydrofuran.

After complete removal of the organic solvent, the reaction mixture containing the compound of formula II is added to the alcohol. It was surprising and unexpected to find that prior removal of the organic solvent from the reaction mixture led to a significant improvement in the yield of the compounds of formula I. In a typical example the yield improved from about 55% to about 96%.

The reaction products having formula I are treated with a suitable base and water to neutralize residual sulfuric acid. Preferably the base is ammonium hydroxide.

In a preferred embodiment, the compound of formula I is 3-[1,3] dioxolan-2-ylidene-3H-indene-1-carbonitrile.

DETAILED DESCRIPTION OF THE INVENTION

The present invention is an improved process for producing compounds of formula I according to the reaction sequence illustrated in Scheme I.

Scheme 1

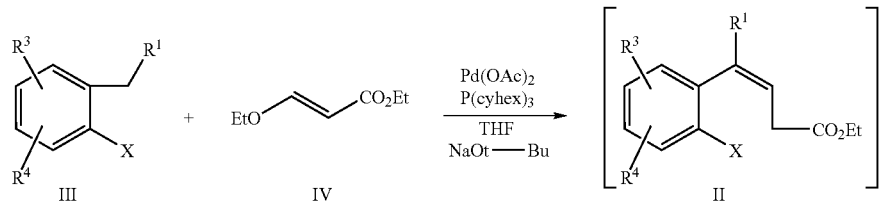

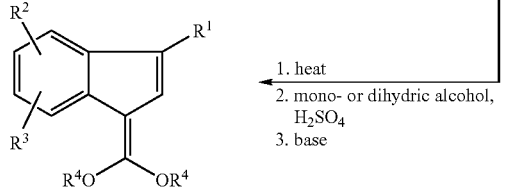

Compound II is produced by the addition reaction of the compound of formula III to the unsaturated ethyl 3-ethoxy acrylate (IV) in the presence of tricyclohexylphosphine, palladium II acetate and a base in an inert water miscible organic solvent, preferably tetrahydrofuran (THF). The reaction proceeds at a temperature between about 58° C. to about 62° C., preferably at 60° C. The reaction is carried out for a period of time of about 3 to about 4 hours; preferably about 3.5 hours.

Compounds of formula II are cyclized and converted into the acetal (I) by reaction with an alcohol and sulfuric acid. Generally a compound of formula II is not isolated prior to conversion into compound I. In a preferred embodiment, compound II is added, without prior isolation, to the alcohol followed by the addition of sulfuric acid. The reaction is conducted at about 35° C. to about 45° C.; preferably at about 40° C., for a period of time of about 6 hours to about 8 hours, preferably about 7 hours.

The process improvement disclosed herein relates to the inert water miscible solvent employed in the reaction leading to compounds having formula II; and, specifically, to removal of the solvent upon completion of the reaction.

When the reaction of compounds of formula II with a monohydric or dihydric alcohol was carried out in the presence of the water miscible organic solvent, the physical state of the reaction mixture became extremely difficult to handle and a substantial quantity of product was lost. Specifically, a large amount of foam was generated due possibly to in situ formation of a surfactant. Furthermore, the product was in a gelatinous state making separation by filtration impractical.

Removal of the inert water miscible solvent prior to the reaction of compounds of formula II with the alcohol eliminated these problems. Solvent removal was a critical step in obtaining product yields of compounds of formula I of at least 90%.

In a preferred embodiment the THF solvent was removed by distillation prior to the addition of compound II to the alcohol. In a preferred embodiment, the alcohol is a dihydric alcohol; and, most preferably the dihydric alcohol is ethylene glycol.

In a preferred embodiment of the present invention, $R^1$ is a nitrile group.

Compounds of formula I wherein $R^1$ is nitrile are useful in the preparation of compounds having the formula

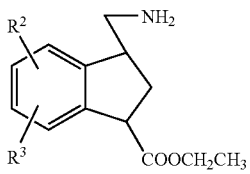

V

As disclosed in U.S. patent application Ser. No. 09/514,002, filed Feb. 25, 2000, compounds of formula V are useful intermediates in the synthesis of certain aryl fused azapolycyclic compounds exhibiting activities in the treatment of neurological and psychological disorders.

Scheme 2 illustrates the conversion of selected nitrile compounds of formula I into compounds of formula V Scheme 2

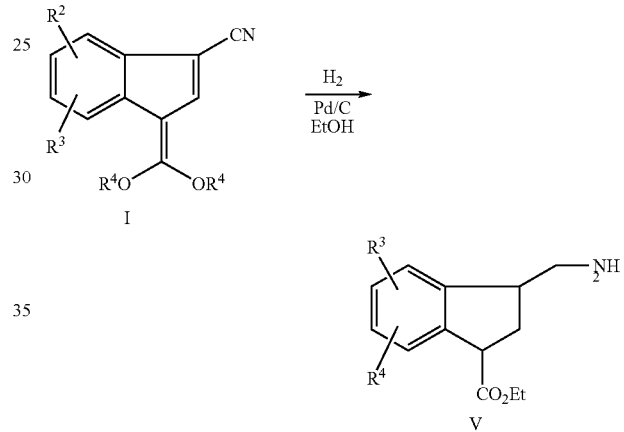

The conversion of compounds of formula V into the aryl fused azapolycyclic compounds of formula is illustrated in Scheme 3.

Scheme 3

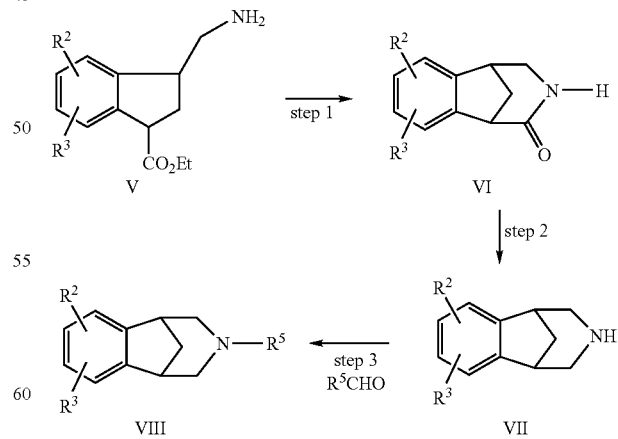

$R^5$ is hydrogen, $C_1$-$C_6$ alkyl, unconjugated $C_3$-$C_6$ alkenyl, benzyl or alkoxy $C_1$-$C_6$.

In step 1 the amine-ester compound of formula V is cyclized with sodium t-butoxide in ethanol to form the nitrogen ring compound of formula VI. The carbonyl function is reduced with sodium borohydride-borontrifluoride giving the aryl fused azapolycyclic compound of formula VII.

Examples of specific compounds of the formula VII are the following compounds:

4-ethynyl-5-chloro-10-aza-tricyclo[6.3.0$^{2,7}$]dodeca-2(7),3,5-triene;

3-trifluoromethyl-10-aza-tricyclo[6.3.0$^{2,7}$]dodeca-2(7),3,5-triene;

4,5-bistrifluoromethyl-10-aza-tricyclo[6.3.1.0$^{2,7}$]dodeca-2(7),3,5-triene;

4-choro-5-trifluoromethyl-10-aza-tricyclo[6.3.1.0$^{2,7}$]dodeca-2(7),3,5-triene;

4-amino-10-aza-tricyclo[6.3.1.0$^{2,7}$]dodeca-2(7),3,5-triene;

4-nitro-10-aza-tricyclo[6.3.0$^{2,7}$]dodeca-2(7),3,5-triene;
4-methyl-10-aza-tricyclo[6.3.0$^{2,7}$]dodeca-2(7),3,5-triene;
4-fluoro-10-aza-tricyclo[6.3.0$^{2,7}$]dodeca-2(7),3,5-triene;
4-trifluoromethyl-10-aza-tricyclo[6.3.0$^{2,7}$]dodeca-2(7),3,5-triene;
4,5-difluoro-10-aza-tricyclo[6.3.0$^{2,7}$]dodeca-2(7),3,5-triene;

Compounds of formula VIII bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of formula VII and their nitrogen substituted derivatives of formula VIII, and their pharmaceutically acceptable salts (hereafter "the active compounds") can be administered via either the oral, transdermal (e.g., through the use of a patch), intranasal, sublingual, rectal, parenteral or topical routes. Transdermal and, oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets may contain a variety of excipients, disintegrants, lubricating agents, and fillers.

Aqueous suspensions for oral administration may be embodied with flavor, coloring matter, and diluent.

For parenteral administration, a solution of the active compound may be suitably buffered and may be diluted with a vegetable oil or propylene glycol.

The following example is provided for the purpose of further illustration and is not intended to limit the scope of the claimed invention.

EXAMPLE

3-[1,3]Dioxolan-2-ylidene-3H-indene-1-carbonitrile

Ethyl 3-ethoxyacrylate (36.9 kg, 255.0 moles), 2-bromophenyl acetonitrile (50 kg, 255. 1 moles), and tetrahydrofuran (57 L) were combined in reactor 1 and the resultant solution was stirred at 25° C. until needed (4 hours.). Palladium II acetate (1.3 kg, 5.7 moles), tricyclohexylphosphine (1.9 kg, 6.7 moles), and tetrahydrofuran (148 L) were combined in reactor 2 and the resultant mixture was stirred for 30 minutes at 25° C. The mixture was then cooled to 5° C. and sodium t-butoxide (61.3 kg, 637.7 moles ) was added to reactor 2 at 5° C. The resulting mixture was warmed to 15° C. and stirred for 15 minutes and then cooled back to 5° C. The contents in reactor 1 were then slowly charged to reactor 2 over 2 hours. at 10° C. and then the contents in reactor 2 were stirred for 15 minutes at 10° C. Reactor 2 was then slowly heated to 60° C. at a rate of 8 to 2° C. per hour (5 hours.) and then held at 60° C. for 4 hours. The reaction was then cooled to 5° C. and ethylene glycol was added at 5° C. The Tetrahydrofuran in the reaction was then distilled off. The reaction was again cooled to 10° C. and sulfuric acid (88.4 kg) added over 1.5 hours at 10° C. The reaction was heated to 40° C. at a rate of 8 to 12° C. per hour (3 hours) and held at 40° C. for 8 hours. The reaction was cooled to 10° C. and ammonium hydroxide (44.8 kg) and water (201 L) were added. The slurry was warmed to 20° C. and granulated for 2 hours. The solid was filtered and washed with water (61 L). The crude solid was recharged to the reactor and water (220 L) added. The slurry was granulated at 20° C. for 4.5 hours and then filtered. The filter cake was washed with water (61 L) and the product dried at 55° C.

The melting point was 227-229° C.

The invention claimed is:

1. An improved process for preparing a compound of the formula

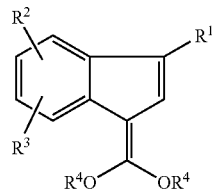

I which comprises: (a) conducting a solvent-free reaction between a compound of formula

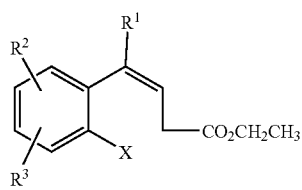

II and a monohydric alcohol of formula $R^4$ OH wherein $R^4$ is $C_1$ to $C_6$ alkyl or a dihydric alcohol wherein said dihydric alcohol is selected from the group consisting of ethylene glycol, 1,3-propylene glycol, and 1,2-propylene glycol, in the presence of sulfuric acid; and (b) treating the reaction product with ammonium hydroxide and water to neutralize residual sulfuric acid;

wherein $R^1$ is an electron withdrawing group selected from the group consisting of cyano, alkoxycarboxyl, alkylcarbonyl, aryl, nitro, trifluoromethyl, and sulfonyl;

$R^2$ and $R^3$ are selected independently from hydrogen, $C_1$-$C_5$ alkyl, $C_1$-$C_5$ alkoxy, trifluoromethyl, halogen, sulfonyl alkyl, alkyamino, amide, ester, aryl-alkyl, and aryl-alkoxy;

and X is selected from the group consisting of chlorine, bromine, and iodine; and wherein said improved process results in about 90% yield and about 80% to 99% in purity of said compound of formula I.

2. The process according to claim 1 wherein said compound of formula II is prepared by (a) reacting a compound of formula III

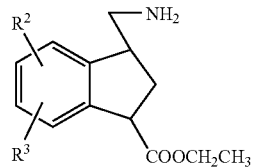

V with ethyl 3-ethoxyacrylate in the presence of a catalyst, wherein said catalyst is a mixture of palladium II acetate, tricylcohexylphosphine and sodium t-butoxide; and an inert water miscible solvent selected from the group consisting of tetrahydrofuran, 2-methyltetrahydrofuran, and 1,2-dimethoxy ethane and (b) completely removing said solvent upon completion of said reaction wherein said solvent is removed by distillation; wherein $R^1$ is an electron withdrawing group selected from the group consisting of cyano, alkoxycarboxyl, alkylcarbonyl, arylcarbonyl, aryl, nitro, trifluoromethyl, and sulfonyl; and X is selected from the group consisting of chlorine, bromine, and iodine; and $R^2$ and $R^3$ are selected independently from hydrogen, $C_1$ to $C_5$ alkyl, $C_1$ to $C_5$ alkoxy, trifluoromethyl, halogen, sulfonyl alkyl, alkyamino, amide, ester, aryl-alkyl, and aryl-alkoxy.

3. The process according to claim 2 wherein said dihydric alcohol is ethylene glycol.

4. The process according to claim 2 wherein said inert water miscible organic solvent is tetrahydrofuran.

5. The process according to claim 1 wherein the compound of the formula I is 3-[1,3] dioxolan-2-ylidene-3H-indene-1-carbonitrile.

6. The process according to claim 1 wherein said dihydric alcohol is ethylene glycol and said base is ammonium hydroxide.

7. The process according to claim 6 wherein said compound of formula I is 3-[1,3] dioxolan-2-ylidene-3H-indene-1-carbonitrile.

8. The process according to claim 2 wherein said catalyst is a mixture of palladium II acetate, tricyclohexylphosphine, and a sodium t-butoxide, said inert miscible solvent is tetrahydrofuran; and wherein said alcohol is a dihydric alcohol selected from ethylene glycol.

9. The process according to claim 8 wherein said compound of formula I is 3-[1,3] dioxolan-2-ylidene-3H-indene-1-carbonitrile.

* * * * *